US008083720B2

United States Patent
Solar et al.

(10) Patent No.: US 8,083,720 B2
(45) Date of Patent: Dec. 27, 2011

(54) DEVICE AND METHOD FOR DELIVERING THERAPEUTIC AGENTS TO AN AREA OF THE BODY

(76) Inventors: Matthew S. Solar, Indialantic, FL (US); Chris Ross, Davie, FL (US); Martin L. Brady, Monkton, MD (US); Raghu Raghavan, Baltimore, MD (US)

( * ) Notice: Subject to any disclaimer, the term of this patent is extended or adjusted under 35 U.S.C. 154(b) by 0 days.

(21) Appl. No.: 12/152,280

(22) Filed: May 13, 2008

(65) Prior Publication Data

US 2009/0287141 A1   Nov. 19, 2009

(51) Int. Cl.
*A61M 5/178* (2006.01)

(52) U.S. Cl. .................................. 604/164.01

(58) Field of Classification Search ............. 604/164.01, 604/44, 96.01, 523
See application file for complete search history.

(56) References Cited

U.S. PATENT DOCUMENTS

| | | | | |
|---|---|---|---|---|
| 3,565,074 A * | 2/1971 | Foti | ............. | 604/164.11 |
| 4,013,074 A | 3/1977 | Siposs | ............. | 604/891.1 |
| 4,692,147 A | 9/1987 | Duggan | ............. | 604/891.1 |
| 5,542,915 A * | 8/1996 | Edwards et al. | ............. | 604/22 |
| 5,792,110 A | 8/1998 | Cunningham | | |
| 5,843,093 A | 12/1998 | Howard, III | ............. | 606/130 |
| 6,190,353 B1 * | 2/2001 | Makower et al. | ............. | 604/95.01 |
| 6,572,593 B1 * | 6/2003 | Daum | ............. | 604/264 |
| 6,999,274 B2 | 2/2006 | Beck et al. | ............. | 360/122 |
| 2004/0068299 A1 | 4/2004 | Laske et al. | | |
| 2004/0082905 A1 | 4/2004 | Solar et al. | ............. | 604/43 |
| 2005/0113805 A1 | 5/2005 | Devellian et al. | | |
| 2007/0060927 A1 * | 3/2007 | Longson et al. | ............. | 606/108 |

OTHER PUBLICATIONS

Mark Dubach, "Accurate Stereotactic Injection by Radially Curved Injection Needles," 1991 Congress of Neurological Surgeons, Neurosurgery vol. 29, No. 1,1991; pp. 144-149.
Wlater Levy & John Oro, "Curved Biopsy Needle for Stereotactic Surgery: A Technical Note," 1984 Congress of Neurological Surgeons, Neurosurgery vol. 15, No. 1,1984; pp. 82-85.
Email dated Dec. 6, 2008, From Raghu Raghavan to Mark A. Litman, subject: More Prior art for the Channel catheter, 6 pgs.
PCT the International Search Report and The Written Opinion of the International Searching Authority for related PCT patent application serial No. PCT/US2009/02919 mailed on Nov. 9, 2009.

* cited by examiner

*Primary Examiner* — Kevin C Sirmons
*Assistant Examiner* — Brandy C Scott
(74) *Attorney, Agent, or Firm* — Mark A. Litman & Associates, PA

(57) ABSTRACT

A device, system and method deliver an agent to a soft mass, such as an area of the body, and more specifically the brain. One aspect includes creation of one or more channels, tunnels or grooves in tissue using a relatively small diameter, minimally-invasive stylet and then removing the stylet prior to infusion. The stylet-created channels become paths of increased hydraulic conductivity, through which the infusate will tend to flow and produce a predictable infusion pattern. Infusate will be carried into these channels with relatively low resistance, and then infuse outward from these channels into the surrounding tissue. By carefully positioning these channels, one can control and modify the preferred paths and duration of distribution.

14 Claims, 3 Drawing Sheets

DEVICE AND METHOD FOR DELIVERING THERAPEUTIC AGENTS TO AN AREA OF THE BODY

BACKGROUND OF THE INVENTION

Field of the Invention

The present invention relates to the field of intra-parenchymal payload or drug delivery to a region of the body, the brain, or a target within the brain.

Drug delivery to the brain may be accomplished by a number of different methodologies. Oral intake of drugs carries them to the brain through the vasculature. Intravenous catheter delivery also uses the vasculature but takes a more direct route. Both methods are systemic in nature and require the therapy to cross the blood brain barrier.

Intra-parenchymal delivery bypasses the blood brain barrier and delivers the payload directly to the desired target.

Implantable pumps provide a means for continuous delivery of a substance or drug and can mechanically deliver drugs over an extended time period both intravenously and intraparenchymally. Non-mechanical (slow dissolving) delivery systems with intermediate time delivery of drugs are also known.

There are a number of therapies for the treatment of brain tissue that require direct infusion of fluids to specific targets within the brain. This is usually accomplished via one or more catheters implanted into the tissue to carry the infusate. However, the distribution of direct intraparenchymal infusion is a function of several variables and can be challenging to predict and to control.

A standard straight catheter with uniform outside diameter provides a single point for infusion at the tip and the distribution is primarily a function of the tissue properties directly surrounding the distal end of the catheter. Infusate will tend to flow back up along the outer surface of the catheter shaft, a phenomenon known as reflux or backflow. This can be a significant problem, in that if the backflow distance is too large, a significant amount of infusate can leak out the brain surface, reducing the intraparenchymal distribution. The length of backflow tends to increase with the catheter's outside diameter and the flow rate. Thus, catheters with smaller diameters are preferable as they tend to reduce the backflow distance as well as the amount of tissue damage around the catheter.

Catheters are usually made from flexible biocompatible materials. In order to avoid bending during insertion, a rigid stylet or obturator is usually inserted into the catheter inner diameter to add stiffness and improve targeting accuracy. The minimum catheter diameter is often limited by this need for rigidity during insertion. Some catheters balance these two requirements by creating steps on the outside diameter increasing in diameter as you move in the proximal direction away from the tip. This provides a very narrow outside diameter at the distal end, limiting tissue damage and backflow near the point of infusion, while allowing greater rigidity in the more proximal portions of the catheter.

While the backflow distance can be significantly affected by catheter diameter, the distribution into tissue is largely dominated by properties of the tissue itself. Wider distribution areas or more complicated distribution geometries can be obtained by inserting multiple catheters. However, this approach increases the complexity of the surgery and the total amount of tissue damage due to the multiple trajectories.

Some catheters attempt to address this problem using multiple ports on a single catheter shaft, in such a manner that the flow through the individual ports can be controlled independently. The shutter and shades (U.S. Pat. No. 6,999,274) design uses several side holes to distribute the infusate. It has an active internal mechanism to selectively infuse through the desired side holes. The distal end is closed so that flow will only exit the chosen ports. While the directability of this design is good at its outer surface, once the infusate leaves the catheter the distribution is primarily a function of the tissue properties and little can be done to direct it.

A multilumen design (U.S. Pat. No. 5,843,093) addresses this issue with microcatheters that protrude outward and may be selectively deployed and extended to reach out further radially from the outer surface of t host catheter. In addition to requiring a relatively large host catheter, the micro catheters remain in place during infusion making for a more traumatic delivery system.

The indexing cell delivery design (US Patent Application 2004/0082905) addresses the host catheter issue by providing for multiple infusions from a single delivery conduit but infusion is still delivered through side holes one deployment at a time.

Implantable drug delivery systems may be used for systemic or local delivery of drugs. Examples of systemic drug delivery include the regulated infusion of insulin into the body tissues for the treatment of diabetes and the infusion of Apomorphine for the treatment of advanced Parkinson's disease. The local delivery of drugs or therapeutic agents has particular application to the treatment of neurological conditions where the blood brain barrier prevents many systemically administered drugs from reaching the desired target, or where the delivery of drugs or therapeutic agents to targets other than the desired target may produce unacceptable side effects. Examples of local drug delivery into the cerebrospinal fluid that surrounds the spinal cord and brain include the intrathecal delivery of opioids for chronic pain control and the intrathecal delivery of baclofen for the treatment of spasticity. Drugs and therapeutic agents may be also delivered directly into the brain parenchyma via a catheter whose discharge portion lies adjacent to a predetermined target. Examples of this type of therapy include the infusion of gamma-aminobutyric acid agonists into an epileptic focus or pathway that will block its transmission, the delivery of cytotoxic agents directly into a brain tumor, and the infusion of neurotrophic agents for the protection and repair of failing or damaged nerve cells.

Intraparenchymal delivery of neurotrophins may be used to treat a variety of neurodegenerative disorders including Parkinson's disease, Alzheimer's disease and Amyotrophic Lateral Sclerosis, and may be also useful in stimulating the repair of damaged neural tissue after injury from trauma, stroke or inflammation.

Examples of drug delivery pumps are shown, for example, in U.S. Pat. Nos. 4,013,074 and 4,692,147, each of which describe drug filled reservoirs located within the pump, which are positioned within a housing that contains a gas such that when the reservoir is filled, the gas is compressed which in turn, provides the pressure to empty the reservoir. In particular, U.S. Pat. No. 4,692,147 describes a battery powered motor driven pump. These systems are highly invasive, need to be physically repaired or replaced over time, requiring another invasive procedure.

There is therefore a need for a catheter for intraparenchymal delivery of fluids that allows greater control of the distribution of the infusate, while limiting the damage to the surrounding tissue.

SUMMARY OF THE INVENTION

The current disclosed technology includes a device, system and method for delivering an agent to a soft mass, such as an area of the body, and more specifically the brain. One concept included within the generic scope of technology herein is to create one or more channels, tunnels or grooves in the tissue using a relatively small diameter, minimally-invasive stylet and then removing the stylet prior to infusion. The stylet-created channels become paths of increased hydraulic conductivity, through which the infusate will tend to flow and produce a predictable infusion pattern. Infusate will be carried into these channels with relatively low resistance, and then infuse outward from these channels into the surrounding tissue. By carefully positioning these channels, one can control and modify the preferred paths and duration of distribution. Because the solid stylet can be much thinner than an infusion catheter, much less tissue damage is expected around the infusion site.

The stylet starts out in a retracted position within the delivery system. Once the system is placed in the desired location, the stylet is extended, creating a tissue track, tunnel or channel. The stylet is then retracted and repositioned to create the required delivery path for the infusate.

The stylet may be straight or have any number of various curved shapes such as arcs of varying radii or helical shapes to create channels in the tissue to deliver therapies to desired areas in the brain. The stylet straightens as it is retracted back into a cannula. The curved stylets can be rotated or otherwise repositioned inside the cannula while retracted and then redeployed in another orientation, or exchanged for other shapes, creating multiple tissue channels. Once the desired distribution pattern is achieved the stylet may be removed and infusion may begin. By manipulating or twisting the stylet (or even inflating a balloon associated with the stylet), a shape may be imposed on the channel to form a designed shape to adjust the function and performance of the channel.

It is possible to deploy the stylet/obturator through the catheter leaving the catheter in place and infusing through it after removing the stylet(s). It may also be desirable to remove the catheter/cannula completely and reintroduce the same or a second catheter into the same channel to begin infusion at a later time.

It may also be desirable to create the channels using a stylet and cannula, remove the stylet, introduce a micro catheter through the inside diameter of the cannula, and then remove the cannula prior to infusion.

DETAILED DESCRIPTION OF THE INVENTION

Figure 1:
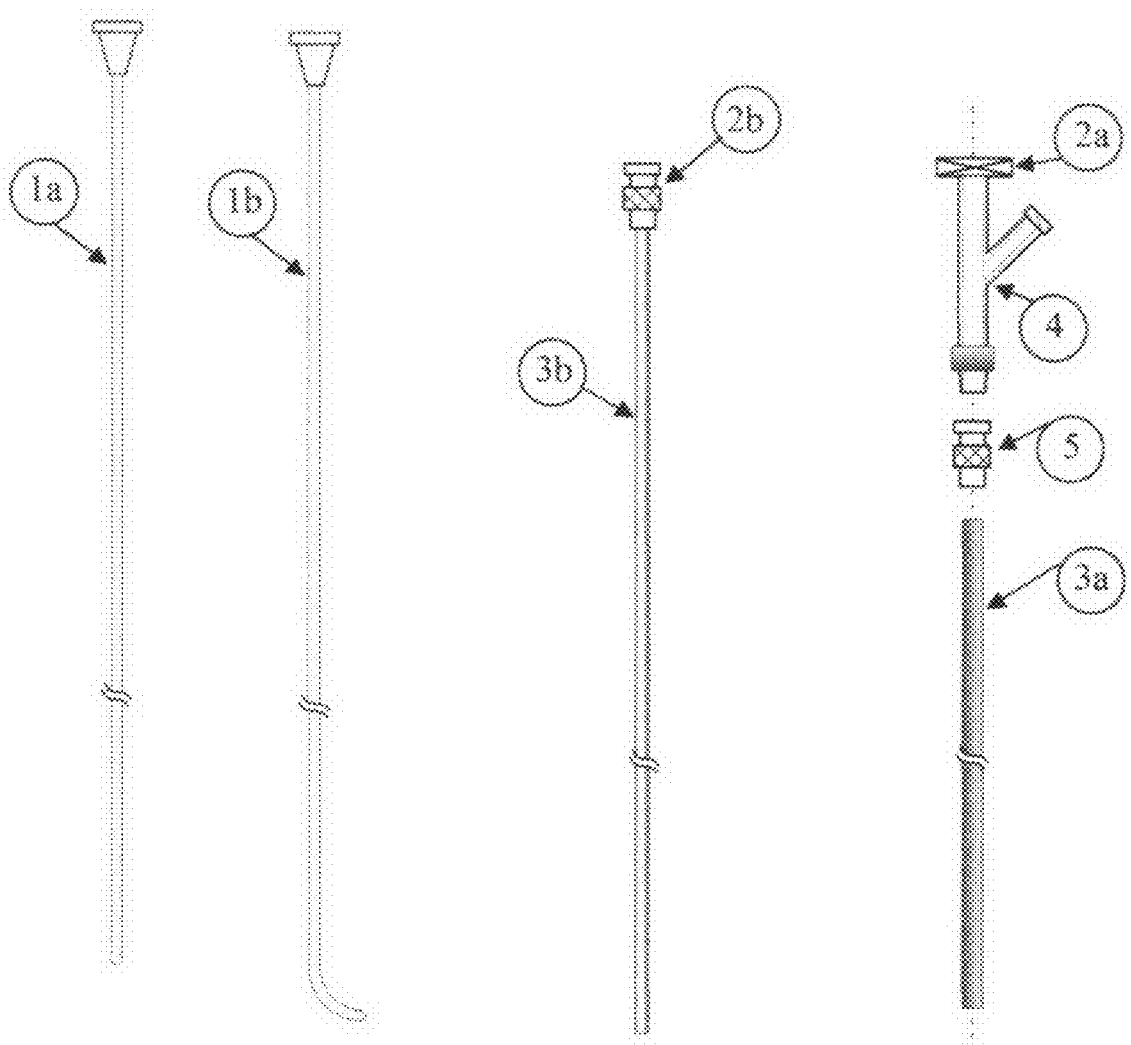
FIG. 1 Shows the straight stylet, the curved stylet, the primary seal, the secondary seal, the catheter, the rigid cannula, the Y-connector and the attachable connector.

After a condition requiring material delivery, such as drug delivery, to a region of the body, particularly to tissue in the brain (where any collateral damage to tissue can be significant) has been diagnosed, and a plan or therapy has been created for delivery of the material or drug (including location, amounts, duration, drug composition, and the like), procedures according to technology described herein may then be performed.

Flow dynamics and mass transfer properties can be analyzed and determined, and local flow and fluid distribution properties can be evaluated as part of the planning process. A size and shape of a final channel is designed and the flow dynamics with specific amounts and types of drugs to be delivered is determined. A catheter size sufficient to carry stylet is provided. A stylet design (cross-section, length, diameter shape, e.g., uniform, gradated, sinusoidal, etc.) is made consistent with the plan, and the stylet positioned within the catheter for delivery. The plan, as previously indicated, may include immediate delivery before, during or after partial or complete removal of the stylet. If drug delivery is before stylet removal, and the drug remains about the opening of the channel created by the stylet, then removal of the stylet will create a reduced pressure area in the channel into which the drug may be drawn. Similar effects occur upon partial removal contemporaneous with drug delivery. By proper flow and pressure analysis, the timing of delivery and stylet removal may also be coordinated to provide the exact methodology to be used in the procedure and plan.

The current disclosed technology includes a device, system and method for delivering an agent to a soft mass, such as an area of the body, and more specifically the brain. One concept included within the generic scope of technology herein is to create one or more channels, tunnels or grooves in the tissue using a relatively small diameter, minimally-invasive stylet and then removing the stylet prior to infusion. The stylet-created channels become paths of increased hydraulic conductivity, through which the infusate will tend to flow and produce a predictable infusion pattern. Infusate will be carried into these channels with relatively low resistance, and then infuse outward from these channels into the surrounding tissue. By carefully positioning these channels, one can control and modify the preferred paths and duration of distribution. Because the solid stylet can be much thinner than an infusion catheter, much less tissue damage is expected around the infusion site. Techniques such as stents, braces, or supports may be deposited in the openings, especially where the stents etc. are biodegradable or even have controlled solubility. This can be used to maintain an opening slightly or greatly beyond the time when elasticity of the soft mass will close the opening and excessively reduce capability of in-flow into the opening. Materials such as sugars (mannitol, rabbitol, etc.) or soluble polymers known to be biotolerable (polyvinyl alcohol, amyloose and amylopectin polymers) may be used as the stent or brace.

Descriptions of the method include at least a method of delivering a substance to an area of the body comprising: inserting a tissue-penetrating device into tissue, removing the tissue penetrating device, thereby creating a channel in the tissue, and delivering the substance into that channel. In general, the tissue penetrating device will have a distal tip capable of penetrating the desired tissue, and may comprise a stylet carried to the tissue by a catheter. After the stylet penetrates the tissue, drug is delivered in a region about the channel formed by the penetration of the stylet. The drug may be delivered while the stylet is at its deepest penetration into the tissue, while the stylet is being withdrawn or has been partially withdrawn from its deepest penetration into the tissue, or the drug is delivered after the stylet has been completely withdrawn from its deepest penetration into the tissue.

At least one channel is created by extending a stylet or obturator at least some distance exterior to a cannula, such as a distance sufficient (or slightly more than sufficient) to cause the depth of penetration desired for the procedure. The direction or alignment of the stylet leaving the cannula may be coaxial with the cannula and coaxial with at least a portion of a trajectory path for insertion of the stylet or obturator into the tissue. The direction or alignment of the at least one channel is created by extending a stylet or obturator at least some distance exterior to a cannula may be coaxial with the cannula at a point to contact with the tissue which is not coaxial with linear path for penetration of the tissue by the stylet or obturator. (That is, at least one channel may be created by extending a stylet with a curved shape (arc, sinusoidal, helical, etc.) from a relatively straight (or arcuate) cannula to create a curved channel. The at least one channel may be created coaxially to the cannula in combination with at least one curved channel.

Another method may be described as for introducing a substance to an area of the body through a cannula without introducing bubbles into the area of the body. This method could include steps wherein the cannula is purged of gases with the substance, a device comprising a stylet or obturator is placed into the cannula, again any bubbles are purged with the substance, the cannula is inserted into the body while maintaining a seal around the stylet, and the stylet or obturator is removed while providing a volumetric flow rate of the substance into the cannula. The volumetric flow rate may comprise delivering a volume of the substance approximately equal to the volume of the stylet or obturator being removed. In this way, the entire volume or a majority of the volume will be filled with the substance as it fills the void left by the stylet removal.

A discussion of the Figures will further enhance an understanding of the generic scope of the present technology. FIG. 1 shows a complete system A for use in the technology of the present disclosure, including alternative elements. The system is shown with 1a) Stylet, Straight—This stylet is straight and may be held flush or slightly protruding from the distal end of the cannula to prevent coring during insertion. It can then be extended and retracted to create a tissue channel. 1b) Stylet, curved—This stylet can have any non-straight shape such as an arc, sinusoidal pattern or helix and be used in the same way as the straight version to create a channel or track in the tissue. 2a) Primary Seal—The primary seal forms a tight liquid seal around the rigid cannula (3b. 2b) Secondary Seal—this may be achieved either by sizing the stylet to the (inner diameter (ID) of the cannula 3b very closely creating a high enough resistance to fluid flow to prevent leakage or by providing a more active seal such as an "O-Ring." 3a) Catheter—The catheter may be rigid or semi-rigid if it is used for an acute delivery or a flexible material if requires chronic delivery and subsequent tunneling of the catheter beneath the scalp. 3b) Rigid cannula—In the case when using a flexible catheter and a curved stylet, the rigid cannula is required to straighten the stylet when retracted. 4) Y-Connector—This is a means to provide a side port to connect an injection source for the infusate. 5) Attachable connector—A liquid tight connector may be attached and removed to provide the ability to inject initially, remove the stylet, cannula, y-connector etc. then tunnel the catheter beneath the scalp and then be reattached once the catheter is tunneled, to allow for connection to resume infusion.

Figure 2:
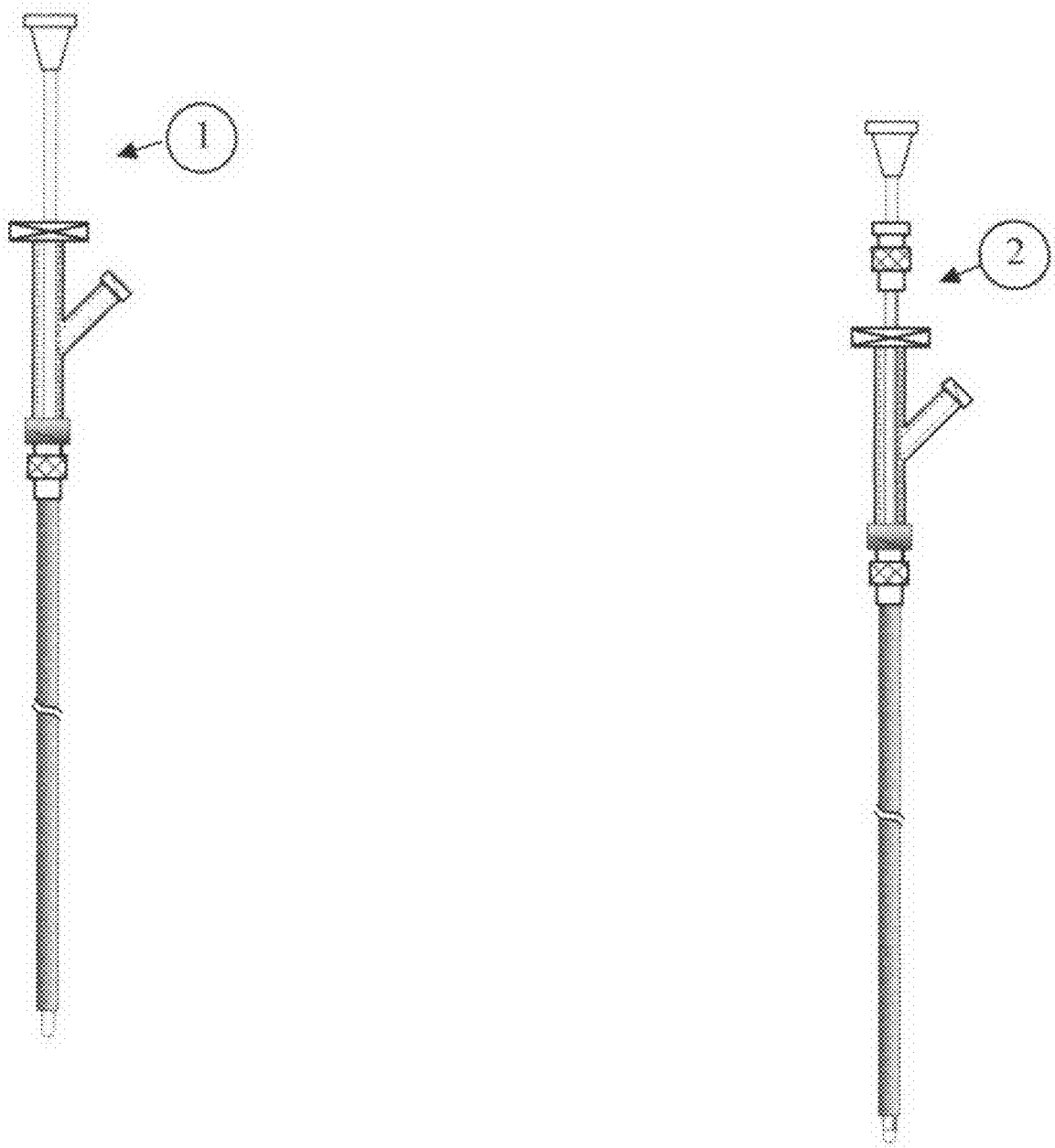
FIG. 2 shows one configuration without a rigid cannula and a second with the rigid cannula.

In FIG. 2, a number, but less than 11 alternative structures is shown. Several combinations are possible.

In a first case there is no separate rigid cannula. The catheter here serves both functions. It could be rigid enough to straighten a curved stylet if needed and provides a conduit for infusate. This could be any one of the following configurations:

a) A flexible catheter with a straight stylet
b) A rigid or semi-rigid catheter with a straight stylet
c) A rigid or semi-rigid catheter with a curved stylet In a second case there is both a rigid cannula and a separate catheter. This could be any one of the following configurations:

d) A flexible catheter with a straight stylet
e) A flexible catheter with a curved stylet
f) A rigid or semi-rigid catheter with a straight stylet
g) A rigid or semi-rigid catheter with a curved stylet Interchangeability of the stylets is also possible.

Figure 3:
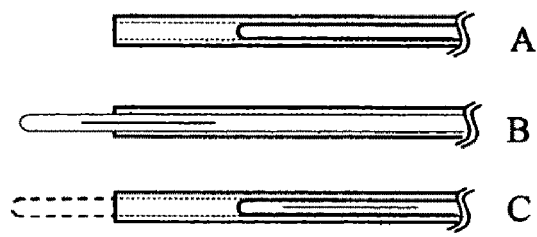
FIG. 3 shows the creation of a straight tissue channel.
Figure 4:
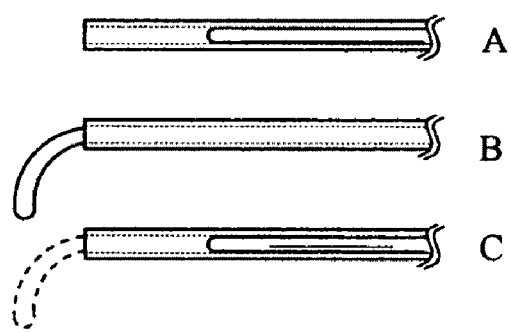
FIG. 4 shows the creation of a curved tissue channel.

FIG. 3 shows some elements that may be used in a plan with a straight stylet. In A), a straight stylet is retracted in a cannula. In B), the stylet is extended and protrudes into tissue. In C), the stylet is retracted leaving a channel or track in the tissue FIG. 4 shows some elements that may be used in a plan with a curved or arcuate stylet.

Figure 5:
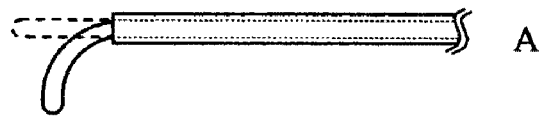
FIG. 5 shows the creation of a combination straight and curved tissue channel.

A) A curved stylet is retracted in the cannula
B) The stylet is extended and protrudes into tissue
C) The stylet is retracted leaving a channel or track in the tissue FIG. 5 shows a system with a combined straight and curved stylet in a catheter.

Figure 6:
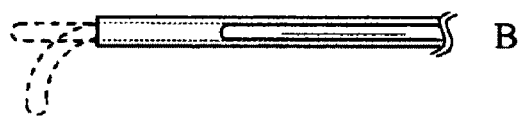
FIG. 6 shows the creation of multiple curved tissue channels in one axial position.

The Figures shows:

A) A straight stylet creates a channel as in 3 above and is exchanged for a curved stylet
B) The curved stylet is retracted leaving a combination straight and curved channel in the tissue FIG. 6 shows enlarging a channel musing a curved stylet. This effect can be done by first following the steps in FIG. 4 using an arc shaped stylet, retracting it into the cannula, rotating it, and then extending it again. In this manner, either multiple channels can be made or an enlarged channel can be made.

Figure 7:
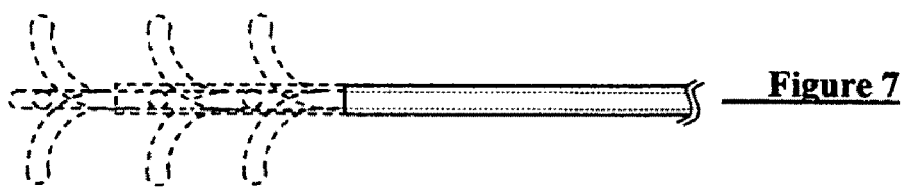
FIG. 7 shows the creation of multiple curved tissue channels in multiple axial positions.

FIG. 7 shows rotating and retracting an arcuate shaped stylet to excavate a larger volume channel in the tissue. This process can be performed by first following the steps in FIG. 6 using an arc shaped stylet, retracting it into the cannula, and then retracting the cannula, extending it again, multiple channels can be made creating the "Christmas tree" array shown in the tissue. Combining arcs with different radii, curved and straight, or other curves such as a helix, several infusion patterns can be created depending on the desired target and therapy.

The design of the stylet could also include a hollow interior and source of materials (e.g., drugs, yes, etc.), power to effect diffusion out of holes in the non-cutting edges and point of the stylet, so that as power is applied, the stylet itself could release the drug or composition to be deposited in the channel. The practice of the technology claimed herein includes methods, systems and devices. Among the concepts disclosed and claimed herein a method of delivering a substance to a region of the body. The method may include inserting a tissue-penetrating device into tissue, removing the tissue penetrating device (preferably without tissue removal, but some tissue sampling for biopsy may be allowed), thereby creating a channel in the tissue, and delivering the substance into that channel. The device used in the method may be a stylet or obturator carried to the tissue by a cannula or catheter. After the stylet penetrates the tissue, drug or marking or image contrast material (hereinafter generally referred to as "drug") is delivered in a region about the channel formed by the penetration of the stylet. The drug may be delivered while the stylet is at its deepest penetration into the tissue or while the stylet is being withdrawn or has been partially withdrawn from its deepest penetration into the tissue, or after the stylet has been completely withdrawn from its deepest penetration into the tissue.

At least one channel may be created by extending a stylet or obturator at least some distance exterior to a cannula that is coaxial with the cannula and coaxial with at least a portion of a trajectory path for insertion of the stylet or obturator into the tissue. Alternatively, at least one channel is created by extending a stylet or obturator at least some distance exterior to a cannula that is coaxial with the cannula at a point of contact with the tissue which is not coaxial with linear path for penetration of the tissue by the stylet or obturator. The method may be practiced wherein at least one channel is created by extending a stylet with a curved shape from a relatively straight cannula to create a curved channel or wherein at least one channel is created coaxially to the cannula in combination with at least one curved channel that is arcuate or helical.

An alternative description of a method according to the technology described herein is for introducing a substance to a region of a body through a cannula without introducing bubbles into the region of the body. This may be accomplished by purging the cannula of bubbles with the substance, placing a device comprising a stylet or obturator into the cannula, again purging any bubbles with additional amounts of the substance, inserting the cannula into the body while maintaining a seal between the stylet and the cannula and then retracting or removing the stylet while providing a volumetric flow rate of the substance into the cannula and out of an outlet from the catheter. In this method, also, providing the volumetric flow rate may be done by delivering a volume of the substance approximately equal (±25%) to the volume of a portion of the stylet or obturator that has been removed from the body.

An alternative description of a method according to the technology described herein is for a method of introducing a substance to a region of soft mass (rubber, elastomer, foam, tree bark and soft tissue, earth, etc.) through a cannula without introducing bubbles, by first inserting a device such as a stylet or obturator in to the cannula, purging any bubbles with the substance, inserting the cannula into the soft mass while maintaining a seal around the stylet, and then retracting or removing the stylet or obturator while maintaining a volumetric flow rate of the substance in to the cannula.

In the methods described herein, non-limiting examples of liquids that may be delivered in the opening created by the stylet are substances selected from the group consisting of a liquid, a drug, cells, and a viral vector.

In these various methods, after insertion of the stylet or obturator, one of the following steps may be performed:

a) only the stylet or obturator is removed and the substance is delivered through the cannula, b) the stylet or obturator and the cannula are removed and replaced by another device for substance delivery, c) one or more curved channels are created by first extending the curved stylet, retracting it, retracting the cannula and stylet together, and then repeating these steps one or more times, d) a device is used to deliver a substance for some finite amount of time and is then subsequently removed or e) the device used to deliver the substance is permanently implanted.

In various practices of the method, the cannula and stylet or obturator may be delivered through a secondary (outer) cannula or catheter, such that when the channel(s) have been created, the first cannula and stylet or obturator are removed and the substance is delivered through the secondary (outer) cannula or catheter. Alternatively, the stylet and cannula are inserted into a secondary, outer cannula or catheter prior to inserting the stylet or cannula into the body, or the stylet and cannula are first inserted into a catheter and the catheter is then purged with the substance prior to inserting the stylet or cannula into the body. The stylet may be used to perform an additional function other than creating the channel, and the additional function is selected from the class of performing diagnostics, taking measurements and delivering therapy prior to being retracted or removed.

A device according to one embodiment of the technology described herein can be used for creating a tissue channel, and the device may include a cannula and a curved stylet that can be straightened by leverage forces, the cannula is sufficiently rigid as to apply leverage force against the curved stylet to straighten the curved stylet when retracted into the cannula. In the device, a seal may be present between the cannula and the stylet to allow for purging of air and/or the cannula and stylet are present within a flexible catheter. The cannula may have a luer that can be removed and reattached to the catheter to facilitate tunneling and/or there is a seal between the cannula and the catheter and a side port in the catheter to purge the air from an interface between the catheter and cannula and back fill the catheter during cannula removal. The stylet may also include a microelectrode, a fiber optic element, a micro coil, an ultrasound transducer or a medical diagnostic device.

Although specific materials, conditions, times, temperatures and other variables may be shown in specificity or even in ranges, those examples and descriptions are not intended to be interpreted as limiting the generic scope of the invention or the claims. One skilled in the art would envision alternatives, equivalents and options without deviating from the generic description of the invention.

What is claimed:

1. A method of delivering a substance to a region of the body comprising:
    inserting a stylet as a tissue-penetrating device into tissue,
    removing the tissue penetrating device, thereby creating a channel in the tissue, and
    delivering the substance into that channel while the stylet is at its deepest penetration into the tissue or after the stylet has been completely withdrawn from its deepest penetration into the tissue;
where the cannula and stylet or obturator are delivered through a secondary outer cannula or catheter, such that when the channel has been created, the first cannula and stylet or obturator are removed and the substance is delivered through the secondary outer cannula or catheter.

2. A method for introducing a substance to a region of a body through a cannula without introducing bubbles into the region of the body comprising:
    purging the cannula of bubbles with the substance,
    placing a device comprising a stylet or obturator into the cannula,
    again purging any bubbles with additional amounts of the substance,
    inserting the cannula into the body while maintaining a seal between the stylet and the cannula and
    then retracting or removing the stylet to form a channel while providing a volumetric flow rate of the substance into the cannula and out of an outlet from the catheter and into the channel;
where the stylet and cannula are inserted into a secondary, outer cannula or catheter prior to inserting the stylet or cannula into the body.

3. A method for introducing a substance to a region of a body through a cannula without introducing bubbles into the region of the body comprising:

purging the cannula of bubbles with the substance,
placing a device comprising a stylet or obturator into the cannula,
again purging any bubbles with additional amounts of the substance,
inserting the cannula into the body while maintaining a seal between the stylet and the cannula and then retracting or removing the stylet to form a channel while providing a volumetric flow rate of the substance into the cannula and out of an outlet from the catheter and into the channel;
where the stylet and cannula are first inserted into a catheter and the catheter is then purged with the substance prior to inserting the stylet or cannula into the body.

4. A method for introducing a substance to a region of soft mass through a cannula without introducing bubbles, by first inserting a device such as a stylet or obturator in to the cannula, purging any bubbles with the substance, inserting the cannula into the soft mass while maintaining a seal around the stylet, and then retracting or removing the stylet or obturator to form a channel while maintaining a volumetric flow rate of the substance in to the cannula and into the channel where a secondary, outer cannula or catheter is first purged with the substance and the stylet is then inserted into the secondary, outer cannula or catheter prior to inserting the stylet or into the body.

5. The method of claim 1 where the stylet is used to perform an additional function other than creating the channel, and the additional function is selected from the class of performing diagnostics, taking measurements and delivering therapy prior to being retracted or removed.

6. The method of claim 2 where the stylet is used to perform an additional function other than creating the channel, and the additional function is selected from the class of performing diagnostics, taking measurements and delivering therapy prior to being retracted or removed.

7. The method of claim 3 where the stylet is used to perform an additional function other than creating the channel, and the additional function is selected from the class of performing diagnostics, taking measurements and delivering therapy prior to being retracted or removed.

8. The method of claim 4 where the stylet is used to perform an additional function other than creating the channel, and the additional function is selected from the class of performing diagnostics, taking measurements and delivering therapy prior to being retracted or removed.

9. The method of claim 1 wherein the substance is selected from the group consisting of a liquid, a drug cells, and a viral vector.

10. The method of claim 2 wherein the substance is selected from the group consisting of a liquid, a drug cells, and a viral vector.

11. The method of claim 3 wherein the substance is selected from the group consisting of a liquid, a drug cells, and a viral vector.

12. The method of claim 4 wherein the substance is selected from the group consisting of a liquid, a drug cells, and a viral vector.

13. The method of claim 1 wherein after the stylet penetrates the tissue, drug is delivered in a region about the channel formed by the penetration of the stylet.

14. The method of claim 2 wherein after the stylet penetrates the tissue, drug is delivered in a region about the channel formed by the penetration of the stylet.

\* \* \* \* \*